United States Patent
Johnson et al.

(10) Patent No.: US 12,426,918 B2
(45) Date of Patent: Sep. 30, 2025

(54) ATRAUMATIC INSTRUMENTS AND ASSOCIATED METHODS FOR CAPSULOTOMY

(71) Applicant: ARTHREX, INC., Naples, FL (US)

(72) Inventors: Matthew Johnson, Bonita Springs, FL (US); Zachary Pharr, Columbia, TN (US); Trenton Boyer, Bonita Springs, FL (US); Jeremy Stephens, Naples, FL (US)

(73) Assignee: ARTHREX, INC., Naples, FL (US)

( * ) Notice: Subject to any disclaimer, the term of this patent is extended or adjusted under 35 U.S.C. 154(b) by 346 days.

(21) Appl. No.: 18/168,653

(22) Filed: Feb. 14, 2023

(65) Prior Publication Data

US 2024/0268858 A1  Aug. 15, 2024

(51) Int. Cl.
*A61B 17/3209* (2006.01)
*A61B 17/32* (2006.01)
*A61B 90/00* (2016.01)

(52) U.S. Cl.
CPC .. *A61B 17/3209* (2013.01); *A61B 17/320016* (2013.01); *A61B 2090/036* (2016.02)

(58) Field of Classification Search
CPC ........ A61B 17/3209; A61B 17/320016; A61B 2090/036; A61B 2090/08021; A61B 17/3211
See application file for complete search history.

(56) References Cited

U.S. PATENT DOCUMENTS

| | | | |
|---|---|---|---|
| 5,029,573 A * | 7/1991 | Chow | A61B 17/34 600/114 |
| 5,224,950 A | 7/1993 | Prywes | |
| 5,792,166 A | 8/1998 | Gordon et al. | |
| 11,266,438 B2 | 3/2022 | Algeri et al. | |
| 11,464,531 B2 | 10/2022 | Brown et al. | |
| 2008/0262525 A1* | 10/2008 | Chang | A61B 17/0218 606/170 |
| 2015/0327882 A1 | 11/2015 | Balek et al. | |
| 2021/0128353 A1 | 5/2021 | Yabe et al. | |
| 2022/0240948 A1 | 8/2022 | Amino | |
| 2022/0265298 A1 | 8/2022 | Michelson et al. | |

FOREIGN PATENT DOCUMENTS

| | | |
|---|---|---|
| CN | 214104538 | 9/2021 |
| EP | 1186282 | 3/2002 |

(Continued)

OTHER PUBLICATIONS

Thaunat, M.D., M., Murphy, M.D., C.G., Chatellard, M.D., R., Sonnery-Cottet, M.D., B., Graveleau, D.D., N., Meyer, M.D., A. and Laude, M.D., F. (2014). Capsulotomy first: A novel concept for hip arthroscopy. Arthroscopy Techniques. vol. 3(5). Oct. 2014. pp. e599-e603.

(Continued)

*Primary Examiner* — Richard G Louis
(74) *Attorney, Agent, or Firm* — Carlson, Gakey & Olds, P.C.

(57) ABSTRACT

This disclosure relates to surgical instruments and methods for incising soft tissue. The instruments may include one or more atraumatic features for reducing a likelihood of trauma to adjacent tissue.

5 Claims, 8 Drawing Sheets

(56) References Cited

FOREIGN PATENT DOCUMENTS

RU         2010558        4/1994
WO     2015069189      5/2015

OTHER PUBLICATIONS

Brochure. CapsuleCut (TM) Blades: Product highlights. Retrieved from: https://www.arthrex.com/sv/resources/product-and-technique-highlights/e8Fxp8F7-0WJSAFZUT3ILQ/capsulecut-blades.
Youtube (2016). Hip joint—Bones, ligaments, blood supply and innervation—Anatomy | Kenhub. Retrieved from: https://www.youtube.com/watch?v=RhDOCdZf1Fk.
Video. Arthroscopic capsulotomy of the hip utilizing the retractable cannulated knife. Retrieved from: https://www.arthrex.com/resources/VID1-00059-EN/arthroscopic-capsulotomy-of-the-hip-utilizing-the-retractable-cannulated-knife.
European Search Report for European Patent Application No. 24157258.5 mailed Jun. 19, 2024.

\* cited by examiner

ATRAUMATIC INSTRUMENTS AND ASSOCIATED METHODS FOR CAPSULOTOMY

BACKGROUND

This disclosure relates to surgical instruments and methods for incising soft tissue.

A surgeon may utilize a surgical instrument to perform a capsulotomy for a patient. Typically, a surgeon will incise the capsule using an instrument with one or more blades to access to the joint space.

SUMMARY

This disclosure relates to instruments and methods for incising tissue. The instruments and methods may be utilized to perform a capsulotomy. The instruments may include one or more atraumatic features for reducing a likelihood of trauma to adjacent tissue.

The disclosed instruments may include a blunt distal tip dimensioned to engage cartilage and other tissue. The instruments may include a catch for engaging and/or retracting tissue. The instruments may include one or more cutting blades. The cutting blades may include cutting edges having respective hooks for incising tissue.

A surgical instrument according to an embodiment may include an elongated main body extending between a proximal end portion and a distal end portion. A tip portion may establish a blunt distal end of the instrument. A cutting portion may interconnect the tip portion and the main body. The cutting portion may include first and second cutting blades on opposite sides of the cutting portion. A minimum width between the first and second cutting blades may be less than a maximum width of an outer periphery of the tip portion.

A surgical instrument according to an embodiment may include an elongated shaft extending along an axis between a proximal end portion and a distal end portion. A tip portion may establish a blunt distal end of the instrument. A cutting portion may include first and second cutting blades having respective cutting edges that may flair outwardly to an outer periphery of the tip portion.

A method of performing a capsulotomy according to an embodiment may include inserting a blunt tip portion of a cutting instrument through an incision and distally of capsular tissue of a patient. The cutting instrument may include first and second cutting blades on opposite sides of a cutting portion that may extend inwardly from the tip portion. The method may include moving at least one of the first and second cutting blades to at least partially separate the capsular tissue.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

This disclosure relates to surgical instruments and methods for cutting soft tissue of a patient. The surgical instruments disclosed herein may be utilized to treat various bones and joints, including bones and joints of the foot, ankle, shoulder, hip and knee. The instruments and methods described herein may be utilized for performing a capsulotomy to incise a capsule of the patient for obtaining access to a joint. The instruments may be utilized in various arthroscopic procedures and joint repairs, such as a labral reconstruction/repair or a cam debridement.

The disclosed instruments may include one or more cutting blades for resecting or incising soft tissue. The cutting blades may be used to separate a capsule for accessing a joint. The disclosed instruments may include a tip portion establishing a blunt distal tip. The blunt geometry may establish an atraumatic surface contour which may avoid or otherwise reduce a risk of trauma to adjacent cartilage, soft tissue and bone of a joint. The tip portion may have various geometries, such as a round or conical profile. The tip portion may be dimensioned to cause the distal tip to deflect off an articular surface of the associated bone in response to over-insertion of the instrument, rather than perforating the articular surface, which may lead to improved healing of the patient. The distal tip of the instrument may protect the cartilaginous surface of the bone, such as a femoral head, which may be deep relative to the capsular tissue and relative difficult to observe. The distal tip of the instrument may protect the surrounding soft tissue, such as the acetabular labrum, in response to over-insertion of the instrument.

The disclosed instruments may include a catch for engaging capsular and other soft tissue. The catch may engage the soft tissue to reduce a likelihood that the instrument may be mistakenly backed out of the joint and slipping past the capsular tissue, which can reduce a risk of trauma to the surrounding tissue and operating time. The catch may be established by a proximal face of the tip portion and may be dimensioned to catch a relatively deep portion of the capsular tissue during a capsulotomy. The catch may be utilized to retract the capsule or other soft tissue.

The cutting blades may include a hook feature for engaging the capsular and other soft tissue. A distal portion of the cutting blade may establish the hook, which may be utilized to hook under and incise the soft tissue, which may reduce operating time to establish the incision.

A surgical instrument according to an embodiment may include an elongated main body extending between a proximal end portion and a distal end portion. A tip portion may establish a blunt distal end of the instrument. A cutting portion may interconnect the tip portion and the main body. The cutting portion may include first and second cutting blades on opposite sides of the cutting portion. A minimum width between the first and second cutting blades may be less than a maximum width of an outer periphery of the tip portion.

In an embodiment, a handle may be coupled to the proximal end portion of the main body.

In an embodiment, the first cutting blade and the second cutting blade may be dimensioned to flair outwardly to the outer periphery of the tip portion.

In an embodiment, the first cutting blade and the second cutting blade may be joined with the outer periphery of the tip portion at a first axial position. The cutting portion may include first and second sidewalls that may interconnect the first and second cutting blades. Each of the first and second sidewalls may include a ridge extending a length of the first and second cutting blades to the outer periphery of the tip portion. The ridge may be joined to the outer periphery of the tip portion at a second axial position. The second axial position may be distal of the first axial position relative to a longitudinal axis of the instrument.

In an embodiment, the tip portion may have a bulbous geometry establishing the distal end of the instrument.

In an embodiment, the tip portion may have a conical geometry that may taper inwardly from the outer periphery to the distal end of the instrument.

In an embodiment, at least one proximal engagement face may be established at a junction between the tip portion and the cutting portion. The at least one proximal engagement face may be dimensioned to slope inwardly from the outer periphery of the tip portion towards the cutting portion.

In an embodiment, the cutting portion may include first and second sidewalls that may interconnect the first and second cutting blades. Each of the sidewalls may include a ridge that may extend a length of the first and second cutting blades. The at least one proximal engagement face may include a plurality of proximal engagement faces that may terminate at junctions with cutting edges of the respective first and second cutting blades.

In an embodiment, a cross section of the cutting portion may have a substantially diamond shaped geometry at a position along a longitudinal axis of the instrument.

In an embodiment, the tip portion and the cutting portion may be symmetrical with respect to a first reference plane and a second reference plane that extend along a longitudinal axis of the instrument. The first reference plane may extend along the first and second cutting blades. The second reference plane may be perpendicular to the first reference plane.

In an embodiment, the distal end may be dimensioned to engage cartilage adjacent to capsular tissue of a patient.

A surgical instrument according to an embodiment may include an elongated shaft extending along an axis between a proximal end portion and a distal end portion. A tip portion may establish a blunt distal end of the instrument. A cutting portion may include first and second cutting blades having respective cutting edges that may flair outwardly to an outer periphery of the tip portion.

In an embodiment, a length may be established between the outer periphery and the distal end of the tip portion relative to the axis. A maximum width of the tip portion may be established across the outer periphery. A ratio of the length divided by the maximum width may be less than or equal to 1:1.

In an embodiment, each of the cutting edges may include a proximal segment, an intermediate segment and a distal segment. The distal segment may slope inwardly from the outer periphery of the tip portion to the intermediate segment.

In an embodiment, a width between the cutting edges may decrease in a direction from an outer periphery of the shaft to the intermediate segment relative to the axis.

A method of performing a capsulotomy according to an embodiment may include inserting a blunt tip portion of a cutting instrument through an incision and distally of capsular tissue of a patient. The cutting instrument may include first and second cutting blades on opposite sides of a cutting portion that may extend inwardly from the tip portion. The method may include moving at least one of the first and second cutting blades to at least partially separate the capsular tissue.

In an embodiment, the cutting instrument may include a proximal engagement face at a junction between the tip portion and the cutting portion. The method may include moving the cutting instrument in a proximal direction such that the proximal engagement face may engage the capsular tissue to oppose proximal movement of the cutting instrument.

In an embodiment, the step of moving the cutting instrument in the proximal direction may include retracting a portion of the capsular tissue in engagement with the proximal engagement face.

In an embodiment, the method may include hooking the capsular tissue with at least one of the first and second cutting blades adjacent to the tip portion of the cutting instrument to at least partially separate the capsular tissue.

In an embodiment, the method may include moving the tip portion into engagement with cartilage adjacent to the capsular tissue.

Figure 1:
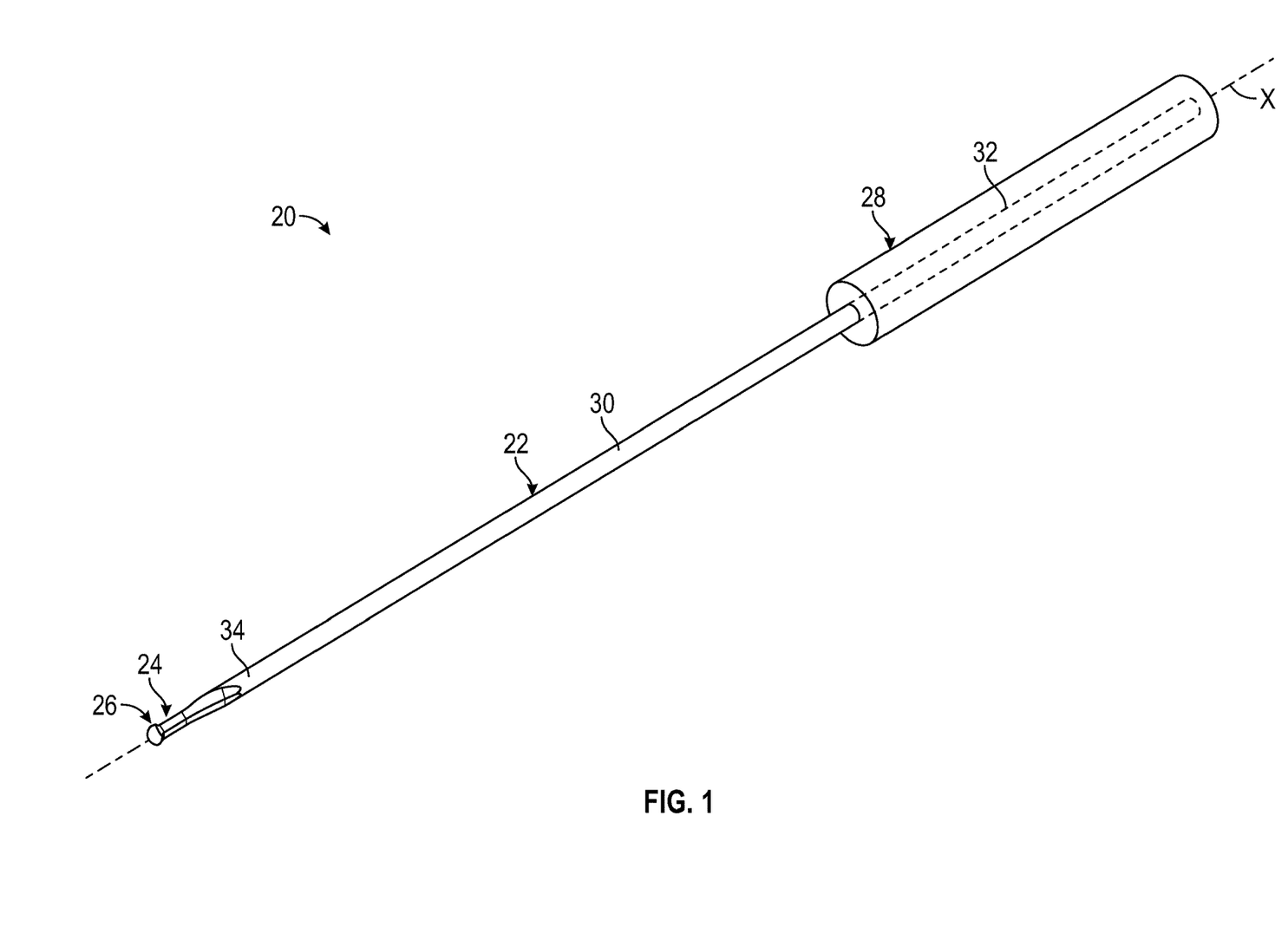
FIG. 1 illustrates a perspective view of a surgical instrument.

FIG. 1 discloses a surgical (e.g., cutting) instrument 20 according to an implementation. The instrument 20 may be utilized for various surgical procedures to cut or otherwise separate soft tissue, such as a capsulotomy to incise and release capsular tissue of a patient. The instrument 20 may be utilized to perform one or more cuts to resect or otherwise remove a portion of the soft tissue. The instrument 20 may include a main body 22, a cutting portion 24 and a tip portion 26. The cutting portion 24 may be dimensioned to interconnect the main body 22 and tip portion 26. The cutting portion 24 may have a straight profile or may have a curved profile to accommodate a geometry of the joint space. The tip portion 26 may establish a terminal (e.g., distal) end of the instrument 20. In implementations, the instrument 20 may include a handle 28. The handle 28 may be adapted for manipulation by a surgeon to position the instrument 20 relative to a surgical site. The instrument 20 may be formed from various materials, including metallic and/or non-metallic materials.

The main body 22 may include an elongated shaft 30. The shaft 30 may extend along an axis X between a proximal end portion 32 and a distal end portion 34 of the main body 22. The axis X may establish a longitudinal axis of the instrument 20. The handle 28 may at least partially receive or may otherwise be coupled to the proximal end portion 32 of the main body 22.

Figure 2:
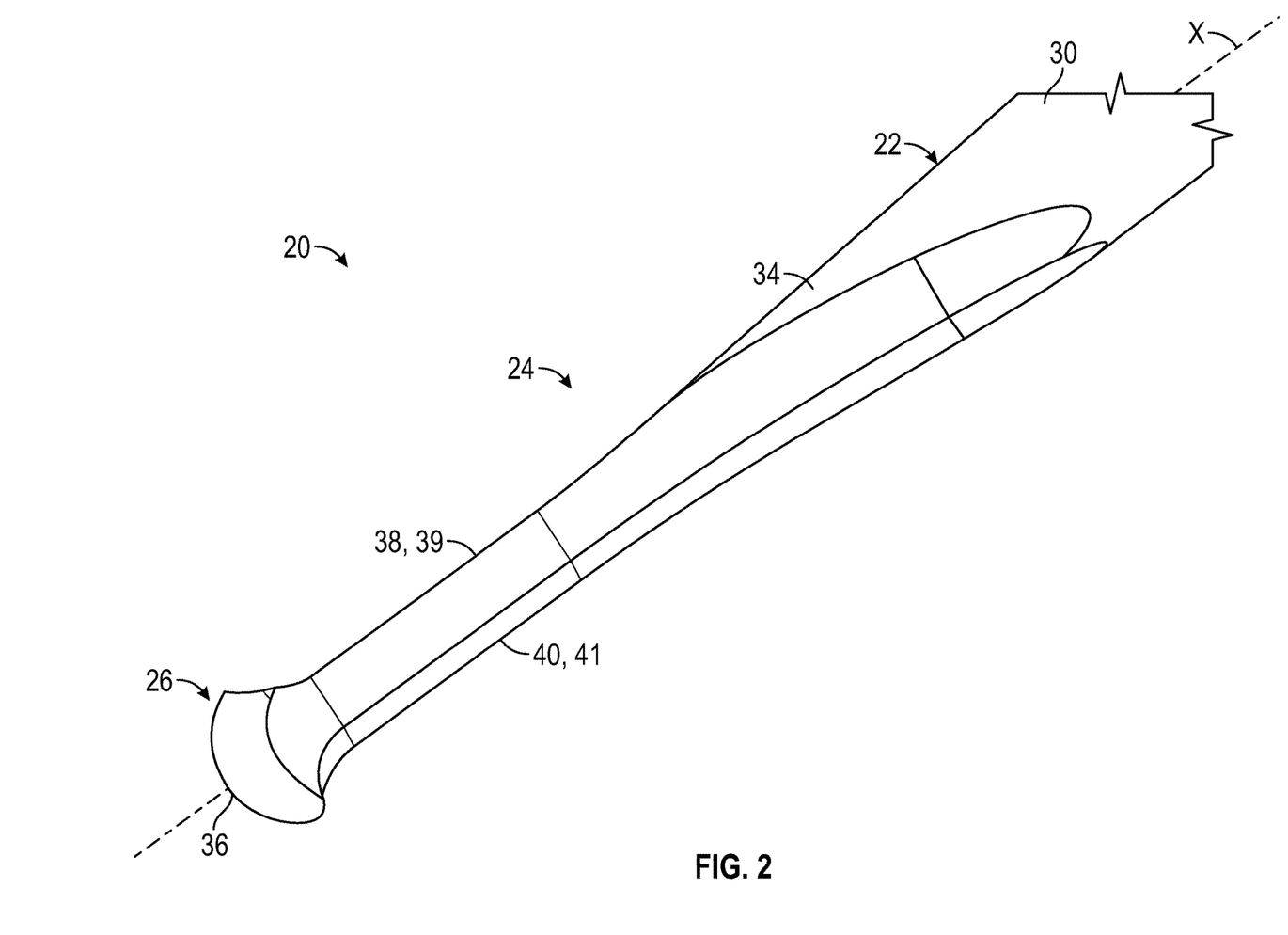
FIG. 2 illustrates a perspective view of a distal portion of the instrument of FIG. 1.

Referring to FIG. 2, with continuing reference to FIG. 1, the instrument 20 may include one or more atraumatic features to limit trauma to bone and/or soft tissue at a surgical site, which can improve healing of the patient. The tip portion 26 may establish a distal end 36 of the instrument 20. The distal end 36 may have a substantially blunt geometry. The distal end 36 may be dimensioned to engage cartilage adjacent to capsular tissue of a patient (see, e.g., FIGS. 10-11). The blunt geometry of the distal end 36 may limit trauma to the cartilage and other tissue.

The cutting portion 24 may include one or more cutting blades dimensioned to cut or otherwise sever soft tissue of a patient, such as capsular tissue adjacent to a joint. The cutting portion 24 may include a first cutting blade 38 and/or a second cutting blade 40. Each of the cutting blades 38, 40 have respective cutting edges 39, 41. The cutting blades 38, 40 may extend axially with respect to the axis X. The cutting blades 38, 40 may be established on opposite sides of the cutting portion 24. Although the instrument 20 is disclosed having two cutting blades, it should be understood that the instrument 20 may include fewer or more than two cutting blades, such as only one cutting blade.

Figure 3:
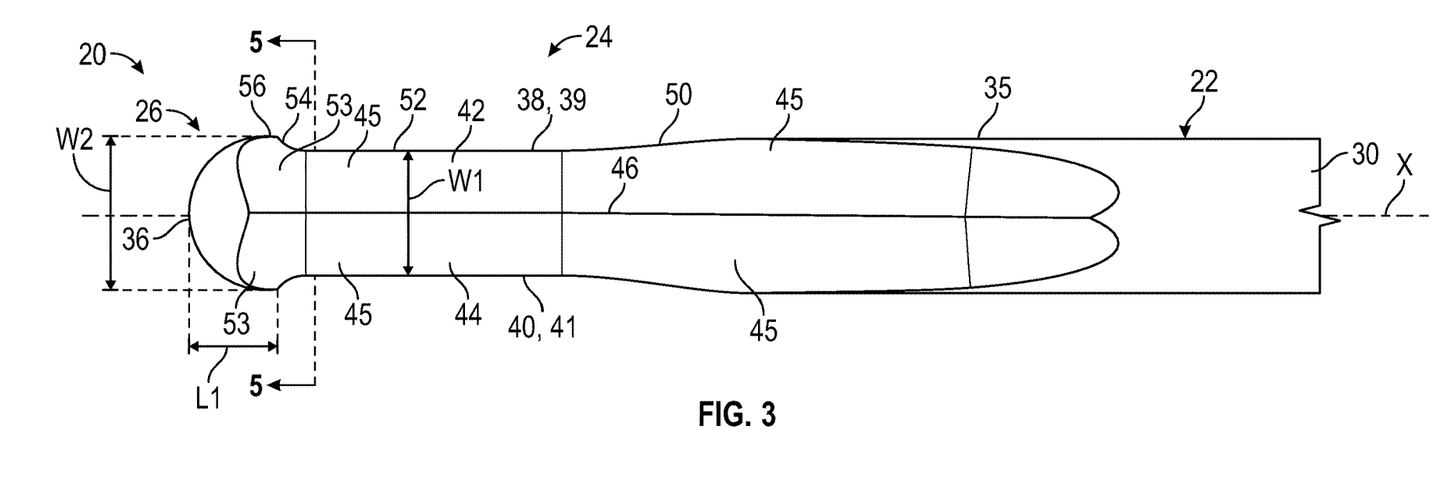
FIG. 3 illustrates a side view of the instrument of FIG. 2.
Figure 4:
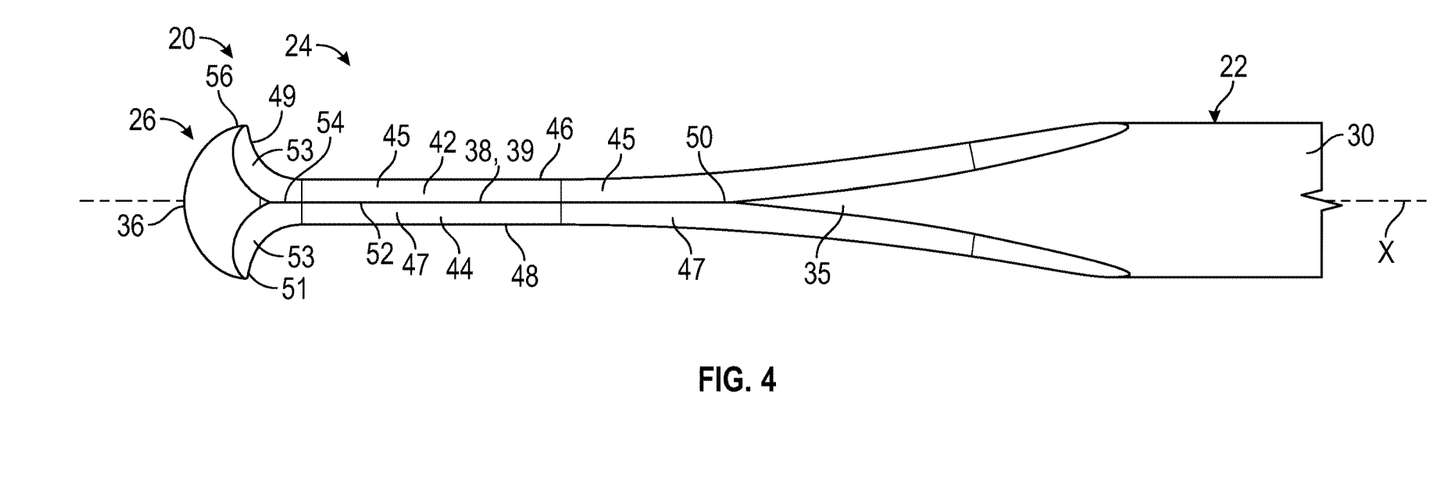
FIG. 4 illustrates another side view of the instrument of FIG. 2.

Referring to FIGS. 3 and 4, with continuing reference to FIG. 2, the cutting portion 24 may include a first sidewall 42 and/or a second sidewall 44. The sidewalls 42, 44 may extend axially with respect to the axis X. The sidewalls 42, 44 may be dimensioned to interconnect the cutting blades 38, 40. The first sidewall 42 may include a first ridge 46. The second sidewall 44 may include a second ridge 48. Each of the ridges 46, 48 may extend a length of the cutting blades 38, 40 relative to the axis X. Each of the sidewalls 42, 44 may include one or more respective facets 45, 47 (see also FIG. 5).

The instrument 20 may include catch features for engaging soft tissue. The instrument 20 may include one or more proximal engagement faces 53 that may be utilized to catch and/or retract soft tissue. The proximal engagement faces 53 may be dimensioned to face towards a proximal end of the instrument 20 relative to the axis X. The proximal engagement faces 53 may be established at a junction between the cutting portion 24 and tip portion 26. The proximal engagement faces 53 may be dimensioned to slope inwardly from the outer periphery 56 of the tip portion 26 relative to the axis X. Proximal engagement faces 53 on opposite sides of the respective ridges 46, 48 may cooperate to establish a catch feature for retracting capsular and other soft tissue adjacent to the tip portion 26. The engagement faces 53 may extend from the facets 45, 47 of the sidewalls 42, 44. The proximal engagement faces 53 may establish a positive stop for engaging the soft tissue. The positive stop may limit a likelihood that the instrument 20 may be unintentionally withdrawn from the joint and proximally past the capsule.

The cutting edges 39, 41 may have various geometries. The cutting edges 39, 41 may be substantially linear along a length of the cutting portion 24. The cutting edges 39, 41 may be curvilinear or may have a complex geometry including one or more segments. In the implementation of FIGS. 3 and 4, each of the cutting edges 39, 41 may include a proximal segment 50, an intermediate segment 52, and a distal segment 54. The intermediate segment 52 may interconnect the proximal segment 50 and distal segment 54. The intermediate segment 52 may be substantially linear such that a width between the cutting edges 39, 41 may be substantially constant at positions relative to the axis X. For purposes of this disclosure, the term "substantially" means ±10 percent of the stated value or relationship unless otherwise indicated. A width between the cutting edges 39, 41 of the cutting blades 38, 40 may decrease in a direction from an outer periphery 35 of the shaft 30 to the intermediate segment 52 of the cutting portion 24 relative to the axis X.

The cutting blades 38, 40 and/or ridges 46, 48 may be dimensioned with respect to an outer periphery 56 of the tip portion 26. The outer periphery 56 may have a substantially elliptical profile (see, e.g., FIG. 5). The cutting edge 39 of the first cutting blade 38 and/or the cutting edge 41 of the second cutting blade 40 may be dimensioned to extend outwardly from the intermediate segment 52 relative to the axis X to establish the distal segment 54 of the respective cutting edges 39, 41. The distal segment 54 may slope inwardly from the outer periphery 56 of the tip portion 26 to the intermediate segment 52 of the respective cutting edge 39/41 (see also FIG. 5). The cutting edge 39 of the first cutting blade 38 and/or the cutting edge 41 of the second cutting blade 40 may be dimensioned to flair outwardly from the intermediate segment 52 to the outer periphery 56 of the tip portion 26 relative to the axis X to establish a hook-shaped geometry, which may be utilized to hook and incise capsular and/or other soft tissue.

A contour of the cutting blades 38, 40 may differ from a contour of the ridges 46, 48 adjacent to the tip portion 26 of the instrument 20. In the implementation of FIGS. 3 and 4, the first cutting blade 38 and/or second cutting blade 40 may be joined with the outer periphery 56 of the tip portion 26 at a first axial position relative to the axis X of the instrument 20. Each of the ridges 46, 48 may extend a length of the first and second cutting blades 38, 40 to the outer periphery 56 of the tip portion 26. The first ridge 46 and/or second ridge 48 may be joined to the outer periphery 56 of the tip portion 26 at a second axial position relative to the axis X. The first and second axial positions may be the same or may differ relative to the axis X. In the implementation of FIGS. 3-4, the second axial position may be distal of the first axial position relative to the axis X such that a distalmost point of the first ridge 46 and/or second ridge 48 may be distal of a distalmost point of the first cutting edge 39 and/or second cutting edge 41 of the respective blades 38, 40. Utilizing the techniques disclosed herein, the ridges 46, 48 may be associated with a relatively more gradual profile than the cutting edges 39, 41 to establish a hook feature for engaging capsular and other soft tissue of a patient.

Referring to FIG. 3, with continuing reference to FIG. 4, the cutting portion 24 may be dimensioned relative to the tip portion 26. A first width W1 may be established between the cutting edges 39, 41 of the cutting blades 38, 40. A second width W2 may be established across the outer periphery 56 of the tip portion 26. The first width W1 may establish a minimum width between the cutting blades 38, 40. The second width W2 may establish a maximum width of the outer periphery 56 of the tip portion 26. In implementations, the first width W1 of the cutting portion 24 may be less than the second width W2 of the outer periphery 56 of the tip portion 26.

The tip portion 26 may be dimensioned to limit trauma to soft tissue of a patient. A first length L1 may be established between the outer periphery 56 and the distal end 36 of the tip portion 26 relative to the axis X. In implementations, a ratio of the first length L1 divided by the second width W2 may be less than or equal to 1:1, or more narrowly between 1:4 and 3:4, inclusive, such that the tip portion 26 is relatively wide relative to its length.

Referring to FIG. 4, with continuing reference to FIG. 3, the ridges 46, 48 may be dimensioned to establish a catch feature for engaging soft tissue. The first ridge 46 may include a first arc segment 49. The second ridge 48 may include a second arc segment 51. The arc segments 49, 51 may have a hook-shaped geometry. The first ridge 46 and/or second ridge 48 may be radiused to establish the respective arc segments 49, 51. The arc segments 49, 51 may have a radius of curvature that may be less than a radius of curvature of the distal segments 54 of the cutting edges 39, 41.

Figure 5:
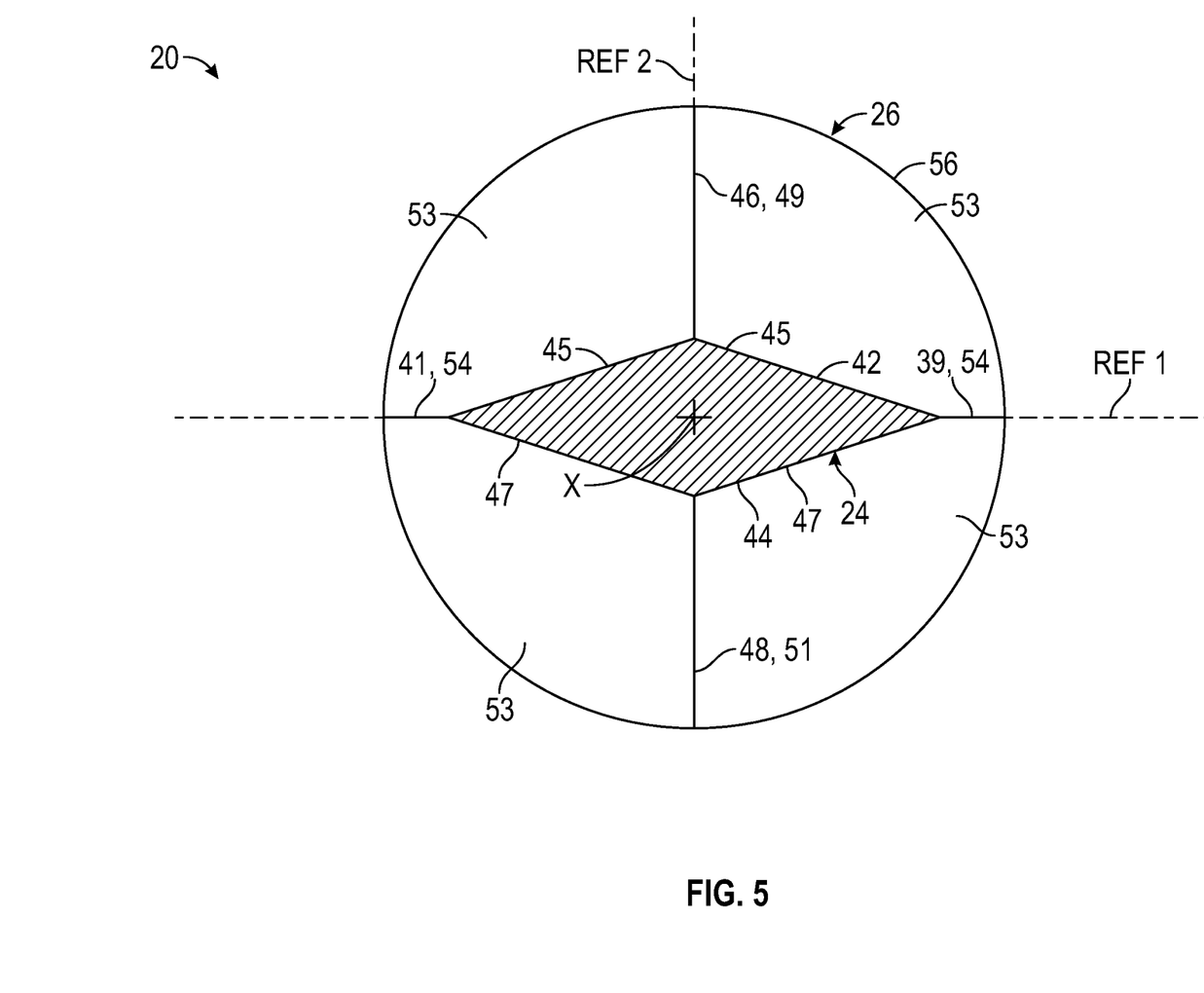
FIG. 5 illustrates a section view of the instrument taken along line 5-5 of FIG. 3.

Referring to FIG. 5, with continuing reference to FIGS. 3-4, a cross section of the cutting portion 24 may have a substantially diamond shaped geometry at a position along the axis X of the instrument 20. The facets 45 may join together at the first ridge 46. The facets 47 may join together at the second ridge 48. A pair of adjacent facets 45, 47 may join together at the cutting edge 39. Another pair of adjacent facets 45, 47 may join together at the cutting edge 41.

In implementations, the tip portion 26 and/or the cutting portion 24 may be symmetrical with respect to a first reference plane REF1 or a second reference plane REF2. The first and second reference planes REF1, REF2 may extend along the axis X of the instrument 20. The first reference plane REF1 may extend along the cutting edges 39, 41 of the cutting blades 38, 40. The second reference plane REF2 may extend along the ridges 46, 48. The second reference plane REF2 may be perpendicular to the first reference plane REF1.

The tip portion may include various geometries to avoid or reduce trauma to adjacent tissue, including cartilage, capsular and other soft tissue of a patient. The tip portion may include a hemispherical geometry and may establish a rounded distal end.

Figure 6:
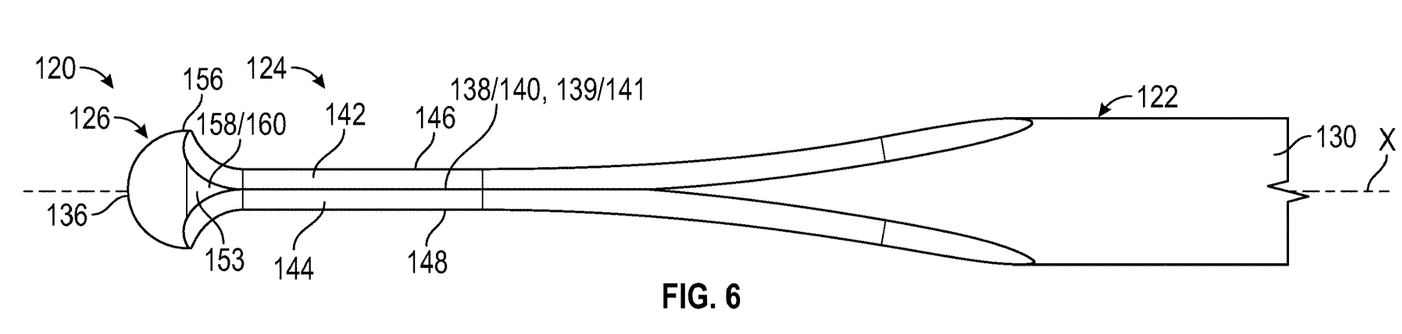
FIG. 6 illustrates a surgical instrument according to another implementation.

FIG. 6 discloses a surgical instrument 120 according to another implementation. A tip portion 126 of instrument 120 may have a substantially bulbous geometry establishing a distal end 136 of the instrument 120. The tip portion 126 may have a substantially hemispherical (e.g., full dome) shape. In implementations, a profile of the tip portion 126 may be established by a constant radius. The instrument 120 may include one or more proximal engagement faces 153 (one shown, and another on an opposite side). The proximal engagement faces 153 may be established at a junction between the cutting portion 124 and tip portion 126. The proximal engagement faces 153 may be dimensioned to slope inwardly from the outer periphery 156 of the tip portion 126 relative to an axis X of the instrument 120. The proximal engagement faces 153 may have a blunt geometry to avoid or otherwise reduce trauma to soft tissue.

In implementations, the proximal engagement face(s) 153 may include a first engagement face 158 and/or second engagement face 160. The engagement faces 158, 160 may be established on opposite sides of the instrument 120 relative to an axis X. In implementations, the first and second engagement faces 158, 160 may have a blunt geometry and may be dimensioned to slope inwardly from the outer periphery 156 of the tip portion 126 towards opposite sidewalls 142, 144 of the cutting portion 124. The engagement faces 158, 160 may be adapted to engage capsular and other soft tissue for limiting or otherwise opposing proximal movement of the instrument 120. In implementations, each of the first and second engagement faces 158, 160 may terminate at junctions with the cutting edges 139, 141 of the respective cutting blades 138, 140. Each engagement face 158, 160 may have a substantially triangular perimeter.

Figure 7:
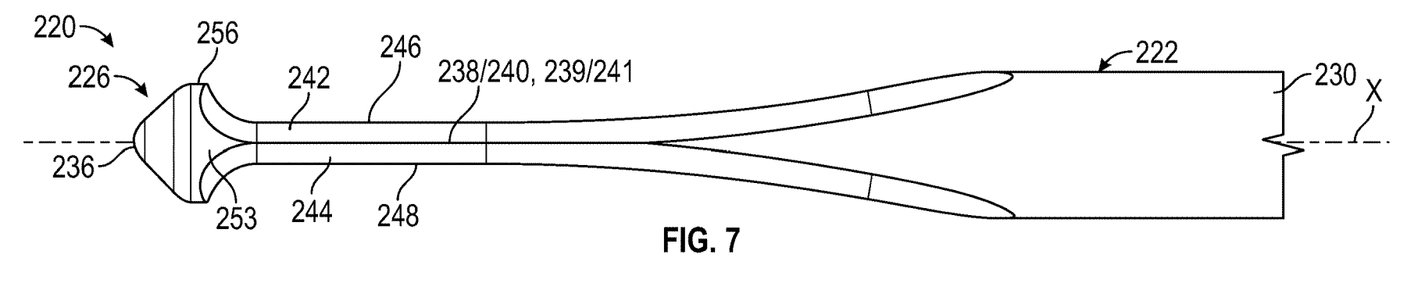
FIG. 7 illustrates a surgical instrument according to another implementation.

FIG. 7 illustrates discloses a surgical instrument 220 according to another implementation. In the implementation of FIG. 7, a tip portion 226 of the instrument 220 may have a conical geometry. The conical geometry may taper inwardly from an outer periphery 256 of the tip portion 226 to a distal end 236 of the instrument 220. The instrument 120 may have an engagement face 253 dimensioned to follow the outer periphery 256. The engagement face 253 may be dimensioned to extend completely about an axis X of the instrument 120. The conical geometry may facilitate insertion of the instrument 220 through a portal in the patient.

Figure 8:
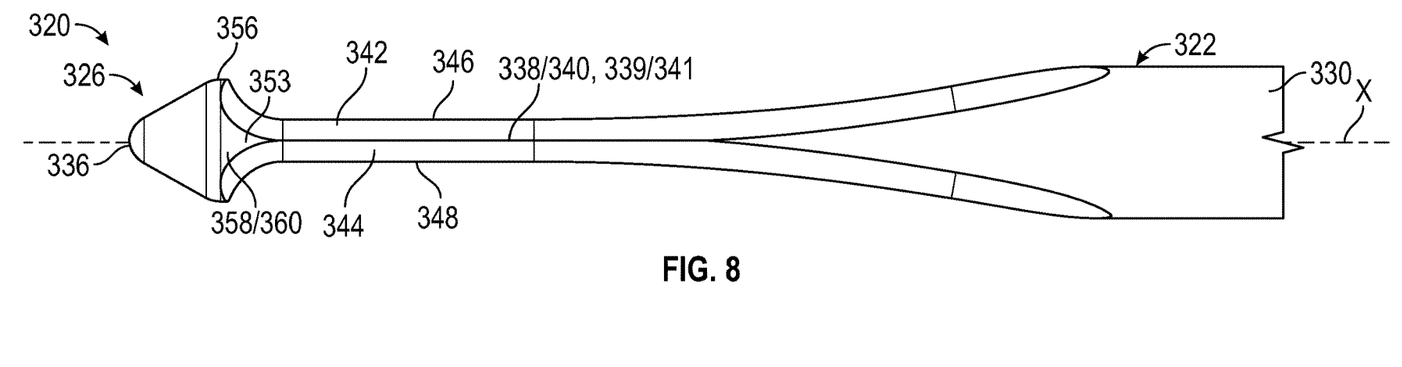
FIG. 8 illustrates a surgical instrument according to yet another implementation.

FIG. 8 illustrates a surgical instrument 320 according to another implementation. In the implementation of FIG. 8, a tip portion 326 of the instrument 320 may have a conical geometry. The conical geometry may taper inwardly from an outer periphery 356 of the tip portion 326 to a distal end 336 of the instrument 320. The tip portion 326 may be relatively longer than the tip portion 226 of FIG. 7 relative to the axis X. A length of the tip portion 226 may be relatively less intrusive inside the joint.

FIGS. 9-12 disclose a method of performing a surgical procedure, such as incising (e.g., cutting) or otherwise separating soft tissue. The method may include establishing one or more cuts to resect or otherwise remove a portion of the soft tissue. The method may utilize any of the surgical instruments disclosed herein. The method may be utilized to perform a capsulotomy for exposing a joint. The surgical instruments disclosed herein may be utilized to treat various bones and joints, including bones and joints of the foot, ankle, shoulder, hip and knee.

Figure 9:
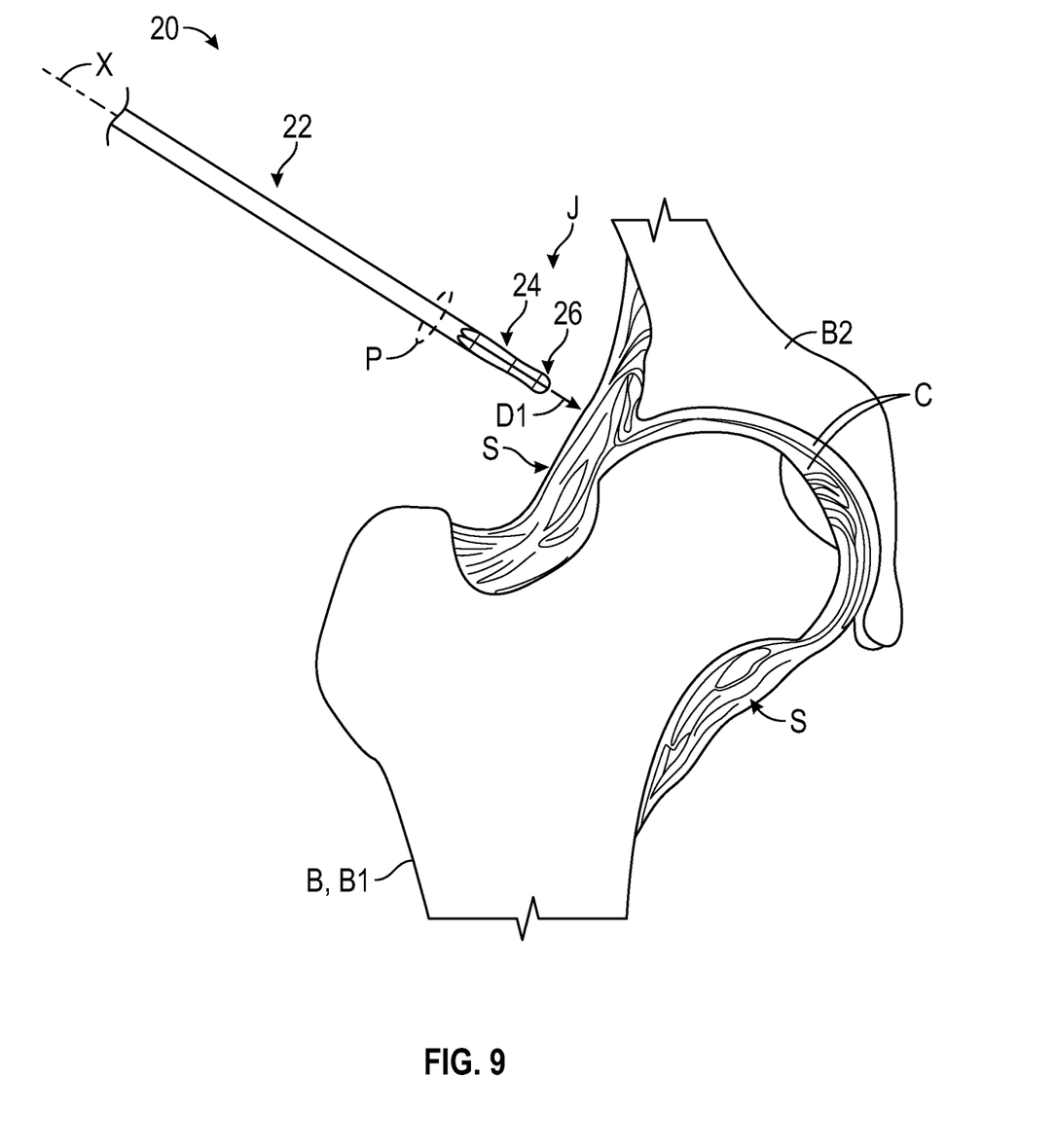
FIG. 9 illustrates a surgical instrument positioned relative to a surgical site.

Referring to FIG. 9, with continuing reference to FIGS. 1-5, the surgeon may move the instrument 20 in a first direction D1 such that at least the cutting portion 24 and tip portion 26 extend through a portal P established in a patient. The portal P may be established by an incision through soft tissue of the patient. In implementations, the cutting portion 24 and tip portion 26 may be passed through a cannula at the portal P.

The tip portion 26 of the instrument 20 may be positioned relative to one or more bones B. The bones B may include a first bone B1 and a second bone B2. Articular surfaces of adjacent bones B1, B2 may establish a joint J. The bones B1, B2 may include a proximal femur and a pelvis that cooperate to establish a hip joint. The bones B may include cartilage C establishing the articular surfaces. The joint J may include soft tissue S. The soft tissue S may include one or more ligaments and capsular tissue.

Figure 10:
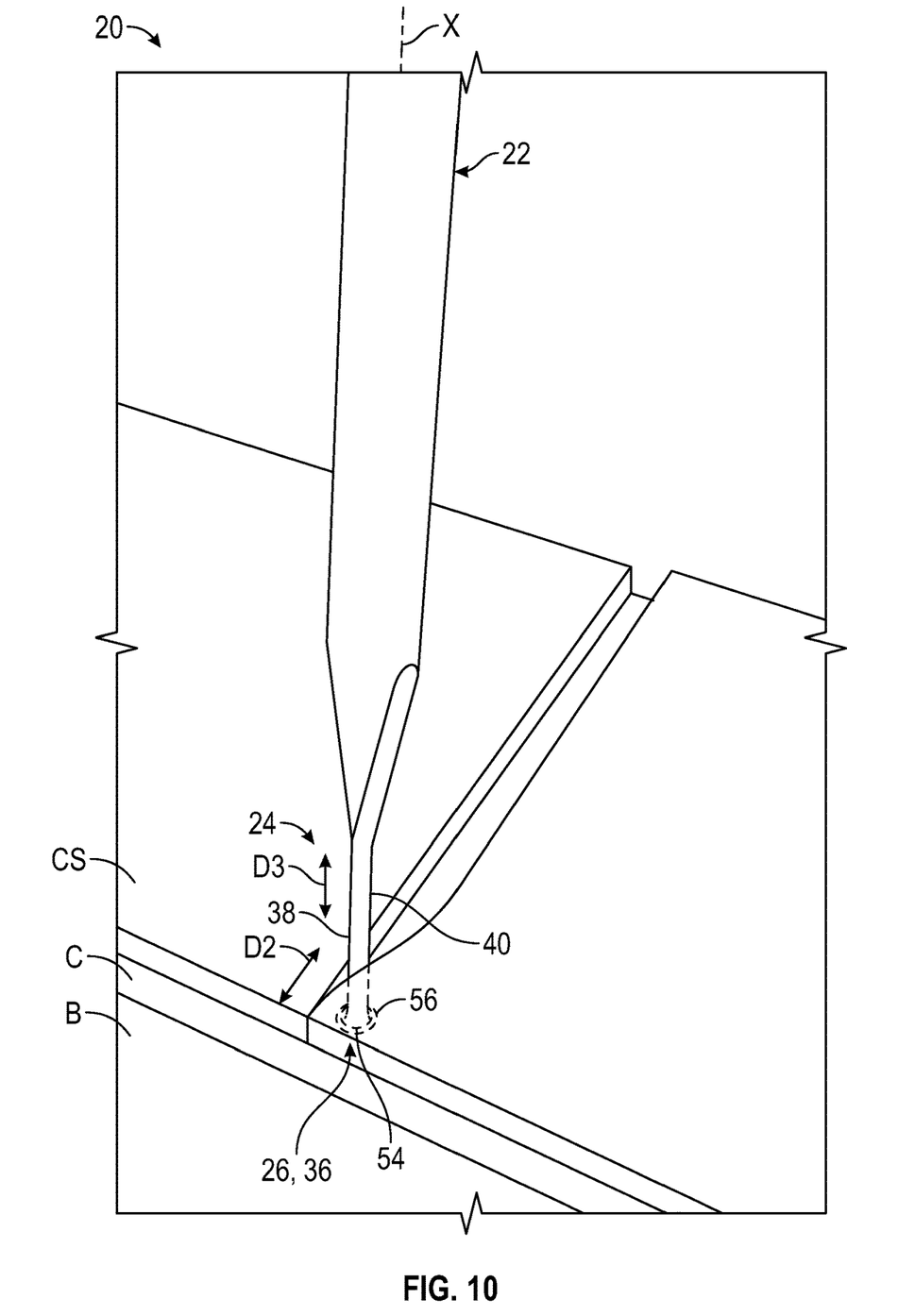
FIG. 10 illustrates a perspective view of the surgical instrument incising tissue of FIG. 9.
Figure 11:
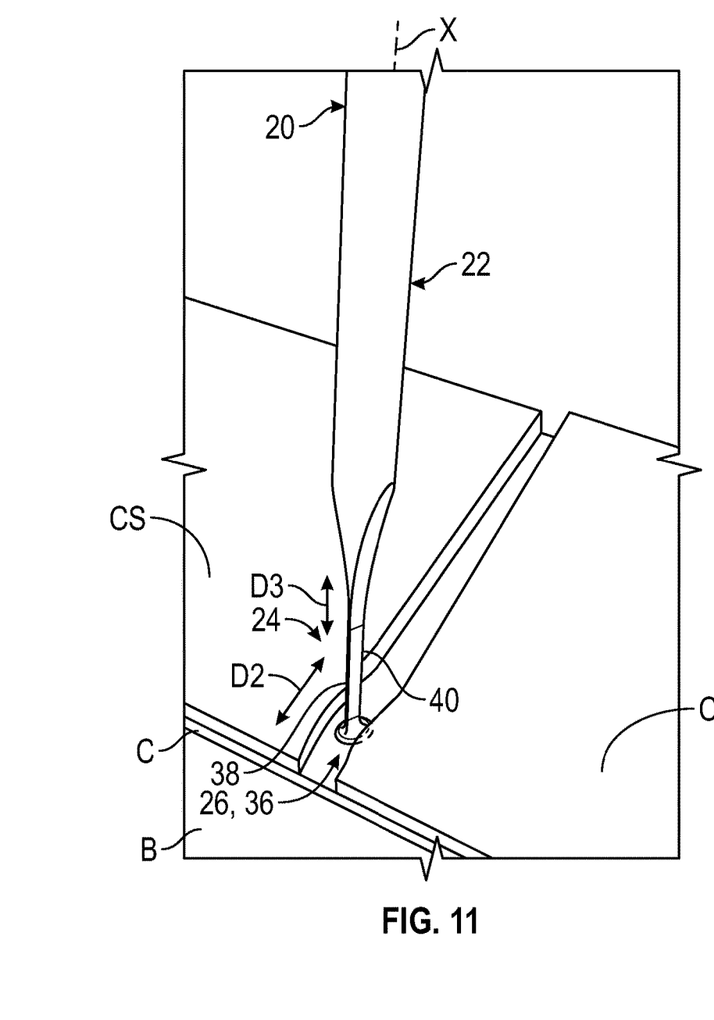
FIG. 11 illustrate another perspective view of the surgical instrument incising the tissue of FIG. 10.

Referring to FIGS. 10 and 11, with continuing reference to FIGS. 1-5 and 9, the blunt tip portion 26 of the cutting instrument 20 may be inserted through the incision at the portal P (FIG. 9) and distally of soft tissue such as capsular tissue CS of the patient. The surgeon may move the tip portion 26 into engagement with cartilage C adjacent to the capsular tissue CS. Utilizing the techniques disclosed herein, the tip portion 26 may avoid or otherwise reduce trauma that may otherwise occur due to engagement with the cartilage C, which may improve healing of the patient. The surgeon may move at least one of the first and second cutting blades 38, 40 in a second direction D2 and/or third (e.g., proximal and/or distal) direction D3 to at least partially cut or otherwise separate the capsular tissue CS of the patient. The surgeon may move the instrument 20 in proximally and/or distally in the third direction D3 (e.g., alternating) to cause the first and/or second cutting blades 38, 40 to incise the capsular tissue CS.

In the implementation of FIG. 10, the surgeon may move the instrument 20 in the second direction D2 and/or the third direction D3 (e.g., proximally and/or diagonally along the cutting path) to hook the capsular tissue CS with the distal segment 54 of at least one of the first and second cutting blades 38, 40 adjacent to the tip portion 26 to at least partially cut or otherwise separate the capsular tissue CS.

The surgeon may perform one or more cuts to resect or otherwise remove a portion of the capsular tissue CS.

Figure 12:
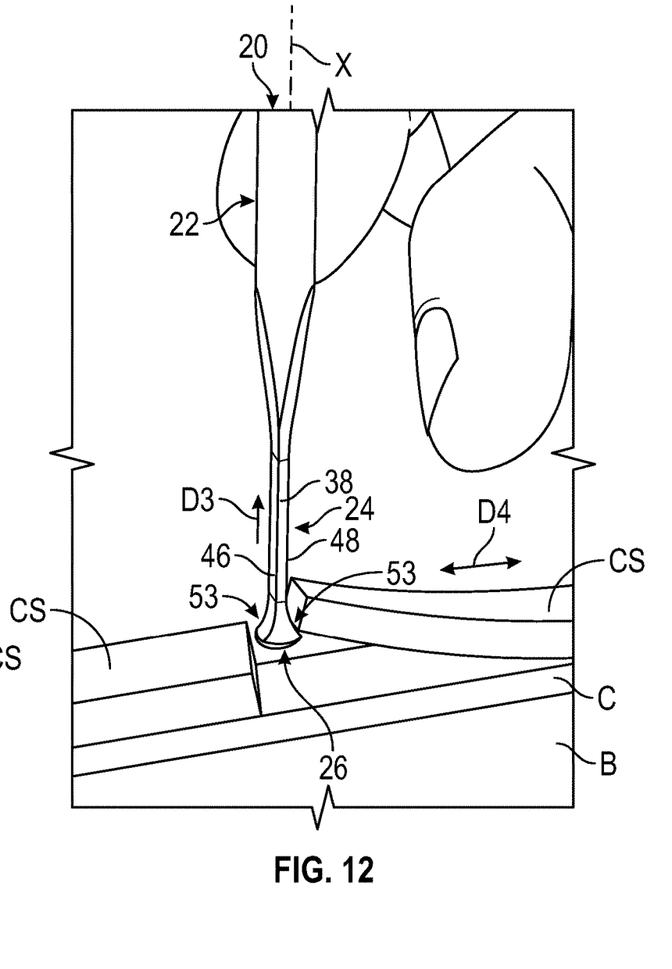
FIG. 12 illustrate perspective view of the surgical instrument retracting the tissue of FIG. 11.

Referring to FIG. 12, with continuing reference to FIGS. 10 and 11, the surgeon may utilizing the instrument 20 to retract soft tissue such as a portion of the capsular tissue CS. The instrument 20 may be positioned such that one or more proximal engagement faces 53 (see also FIGS. 3-5) catches or otherwise engages the capsular tissue CS. The surgeon may move the instrument 20 in the third direction D3 and/or fourth (e.g., lateral) direction D4 (e.g., diagonally from the cutting path) such that the proximal engagement face 53 engages the capsular tissue CS to limit or otherwise oppose proximal movement of the cutting instrument 12. In the implementation of FIG. 10, a width of the outer periphery 56 is greater than a width of a leading portion of the incision, which may reduce a likelihood of the instrument 20 from moving proximally past the capsular tissue CS. The surgeon may continue moving the instrument 20 in the third and/or fourth directions D3, D4 to cause the instrument 20 to retract a portion of the capsular tissue CS in engagement with the proximal engagement face 53.

The novel instruments and methods of this disclosure provide techniques for incising soft tissue in an atraumatic manner. The disclosed instruments may be utilized to resect or otherwise remove a portion of soft tissue. The disclosed instruments may include a blunt distal tip to reduce a likelihood of trauma to cartilage adjacent to the soft tissue. The disclosed instruments may include a catch for reducing a likelihood that the instrument may be unintentionally backed out of the joint and slipped past the capsular tissue. Utilizing the techniques disclosed herein, a risk of trauma to the surrounding tissue may be reduced, which may improve patient healing, and may reduce operating time associated with positioning the instrument. The catch may be utilized to retract the capsule or other soft tissue, which can improve exposure to the joint and reduce operating time.

The disclosed instruments may include cutting blades having a hook for engaging the capsular and other soft tissue. The surgeon may utilize the hook for hooking under and incise the soft tissue, which may reduce operating time to establish the incision.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method of performing a capsulotomy comprising:
   inserting a blunt tip portion of a cutting instrument through an incision and distally of capsular tissue of a patient, wherein the cutting instrument includes first and second cutting blades on opposite sides of a cutting portion that extend inwardly from the tip portion; and
   moving at least one of the first and second cutting blades to at least partially separate the capsular tissue.

2. The method as recited in claim 1, wherein the cutting instrument includes a proximal engagement face at a junction between the tip portion and the cutting portion, and further comprising:
   moving the cutting instrument in a proximal direction such that the proximal engagement face engages the capsular tissue to oppose proximal movement of the cutting instrument.

3. The method as recited in claim 2, wherein:
   the step of moving the cutting instrument in the proximal direction includes retracting a portion of the capsular tissue in engagement with the proximal engagement face.

4. The method as recited in claim 1, further comprising:
   hooking the capsular tissue with at least one of the first and second cutting blades adjacent to the tip portion of the cutting instrument to at least partially separate the capsular tissue.

5. The method as recited in claim 1, further comprising:
   moving the tip portion into engagement with cartilage adjacent to the capsular tissue.

* * * * *